United States Patent [19]

Johnsen et al.

[11] Patent Number: 5,749,730
[45] Date of Patent: May 12, 1998

[54] DENTAL ORGANIZER FOR LIGHT-SENSITIVE MATERIALS

[75] Inventors: James B. Johnsen, Beaverton; Hal J. Oien, Ashland, both of Oreg.

[73] Assignee: Jordco, Inc., Beaverton, Oreg.

[21] Appl. No.: 604,114

[22] Filed: Feb. 20, 1996

[51] Int. Cl.$^6$ ........................................... A61C 3/00
[52] U.S. Cl. ........................ 433/163; 433/77; 206/63.5
[58] Field of Search .................................. 433/9, 77, 25, 433/79, 163; 206/63.5, 368, 369, 823; 220/526, 335; 224/218, 217

[56] References Cited

U.S. PATENT DOCUMENTS

| | | | |
|---|---|---|---|
| 895,124 | 8/1908 | Sundee | 220/335 |
| 3,275,329 | 9/1966 | Lieberman et al. | 220/526 |
| 4,349,632 | 9/1982 | Lyman et al. | 220/335 |
| 4,375,863 | 3/1983 | Kappler | 220/335 |
| 4,694,956 | 9/1987 | Sims | 220/335 |
| 4,822,280 | 4/1989 | Rider | 433/229 |
| 4,898,276 | 2/1990 | Georgakis | 206/369 |
| 4,991,759 | 2/1991 | Scharf | 224/217 |
| 5,106,297 | 4/1992 | Discko, Jr. | 433/77 |
| 5,139,188 | 8/1992 | Scharf | 224/217 |
| 5,199,567 | 4/1993 | Discko, Jr. | 206/369 |
| 5,246,105 | 9/1993 | Eykmann et al. | 206/63.5 |
| 5,249,963 | 10/1993 | McGarrigle | 433/163 |
| 5,257,721 | 11/1993 | Smith et al. | 220/335 |
| 5,377,823 | 1/1995 | Steen et al. | 206/63.5 |
| 5,456,361 | 10/1995 | Walsh et al. | 206/63.5 |

*Primary Examiner*—Cary E. O'Connor
*Attorney, Agent, or Firm*—Kolisch, Hartwell, Dickinson, McCormack & Heuser

[57] ABSTRACT

A dental organizer is provided which includes an opaque base having plural wells configured to contain light-sensitive materials and an opaque cover pivotally coupled with the base so as to protect light-sensitive materials both from spillage and from exposure to light. The cover is configured to engage the base when in a closed orientation, such cover including a plurality of projecting plugs which mate with the wells to seal the onboard light-sensitive materials in the wells. A resilient hinge is mounted intermediate the base and cover, such hinge accommodating pivotal opening and closing of the cover relative to the base. The hinge typically is configured to bias the cover toward an open orientation wherein the cover defines an acute angle relative to the base so as to at least partially shade the onboard materials from light.

18 Claims, 1 Drawing Sheet

DENTAL ORGANIZER FOR LIGHT-SENSITIVE MATERIALS

TECHNICAL FIELD

The present invention relates generally to dental organizers, and more particularly, to an opaque dental organizer which includes a multi-well mixing tray having a flip-up cover configured to protect onboard light-sensitive materials from inadvertent mixture and/or exposure to light.

BACKGROUND ART

For a number of years now, dental practice has involved the use of specialized resins and bonding agents which are applied to a patient's teeth and then cured under intense light. These light-sensitive materials typically are cured using a hand-held light unit which directs radiant energy into the oral cavity, and toward the resins or bonding agents therein contained. Dentists and dental technicians thus are able to rapidly apply the desired resin or bonding agent, and then remove the excess before the material is cured. Unfortunately, however, such light-sensitive materials also may be cured inadvertently upon prolonged exposure to visible light of the type which is normally present in a dental office. Dentists therefore must take care not to expose light-sensitive resins and bonding agents even to ambient light until such materials are to be cured.

In an attempt to avoid inadvertent curing, light-sensitive materials often are stored in opaque containers which shield the materials from light until just prior to use. Upon beginning a procedure, the dentist or dental technician pours a small quantity of the required materials from the opaque containers into a dispensing tray, the dispensing tray typically including a plurality of storage wells. The storage wells typically are configured for receipt of the various materials in quantities appropriate for an individual patient's use. Thereafter, the materials are applied to the patient using an applicator brush, often after being combined in an onboard mixing well. Such dispensing trays, however, do little to shield materials from light once the dental procedure begins. This, in turn, can lead to curing of the materials before they are applied to the patient, impacting on the procedure's effectiveness, wasting expensive materials and wasting the dentist's time. A typical dispensing tray is shown, for example, in U.S. Pat. No. 5,106,297 to Discko, Jr., the disclosure of which is incorporated herein by this reference.

To address these problems, dentists and dental technicians have in the past endeavored to set aside the necessary materials for a procedure at some time prior to beginning the procedure itself. This typically saves time during the procedure, and may help to ensure that the proper materials are available for the dentist's use. Further, materials may be poured into a dispensing tray early in the day, and shielded with an opaque cover until the dental procedure begins so as to protect the materials from contamination or unwanted light.

One dispensing tray which is configured for such preloading is shown in U.S. Pat. No. 4,822,280 to Rider, which discloses a dispenser having drawers with sliding opaque covers. A dispensing tray with an opaque flip-up cover similarly is shown in U.S. Pat. No. 5,249,963 to McGarrigle. Both of these dispensing trays shield onboard light-sensitive materials from visible light until the cover is opened or removed. Neither protects onboard materials from exposure to light once a procedure begins. The disclosures of these patents are incorporated herein by this reference.

Another difficulty which is encountered by users of conventional dispensing trays relates to the potential for spilling onboard materials upon moving or tilting of the tray. It will be appreciated, for example, that some of the materials which are commonly used in dental procedures have a relatively low viscosity, and thus are susceptible to spilling onto the floor, or into an adjoining well where it may undesirable mix with another material. Further, conventional dispensing trays fail to provide users with the instruments which are necessary to mix and apply the materials which such dispensing trays contain.

What is needed is a dispensing tray in the form of a dental organizer adapted to protect onboard light-sensitive materials from exposure to light even when the materials are being applied. It also would be desirable to provide a dental organizer configured to carry such light-sensitive materials in sealed wells, and to carry corresponding instruments for use in mixing and applying the materials to the patient's teeth.

DISCLOSURE OF THE INVENTION

To address the aforementioned objectives, a dental organizer is herein proposed, such organizer including an opaque base with plural wells configured to contain light-sensitive materials, and an opaque cover which is pivotally coupled with the base so as to protect such light-sensitive materials both from spillage and from exposure to light. The cover is configured to engage the base when in a closed orientation, such cover including a plurality of projecting plugs which mate with the wells to seal the wells with the onboard light-sensitive materials in place. A resilient hinge is mounted intermediate the base and cover to accommodate pivotal opening and closing of the cover relative to the base. The hinge typically is configured to bias the cover toward an open orientation wherein the cover defines an acute angle relative to the base so as to at least partially shade the onboard materials from light.

In a preferred embodiment, the base further defines one or more elongate channels, each configured to receive instruments such as applicator brushes. The instruments are held in place by the organizer's cover which typically closes to capture the instruments within the channels. The proposed dental organizer thus may be made patient-specific, each organizer carrying both the materials and instruments necessary to performing a dental procedure in accordance with the particular patient's needs. Further, the organizer may include a notation surface which provides the dentist or dental technician with a surface on which patient information may be transcribed. This helps to identify each patient's organizer relative to other organizers which may be stored close by. It therefore is possible to prepare dental organizers for a number of patients early in the day, and then simply select the appropriate organizer at the time of the procedure.

These and additional objects and advantages of the present invention will be more fully appreciated upon consideration of the drawings in conjunction with the detailed description of the preferred embodiment which follows.

DETAILED DESCRIPTION OF THE PREFERRED EMBODIMENT AND BEST MODE OF CARRYING OUT THE INVENTION

Figure 1:
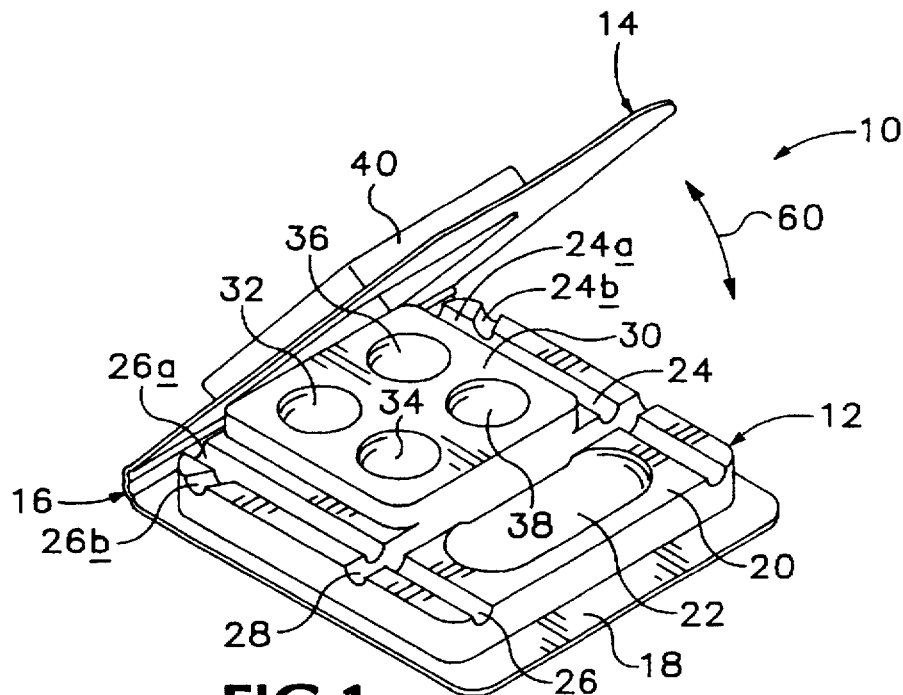
FIG. 1 is an isometric view of a dental organizer formed in accordance with a preferred embodiment of the invention, the dental organizer being shown with its cover in an open orientation.
Figure 2:
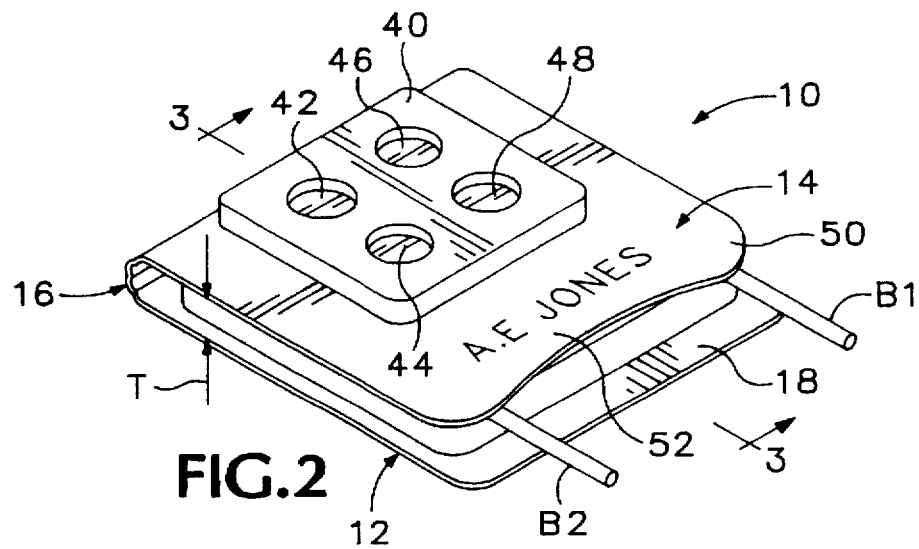
FIG. 2 is an isometric view of the dental organizer shown in FIG. 1, but with the cover in a closed orientation.
Figure 3:
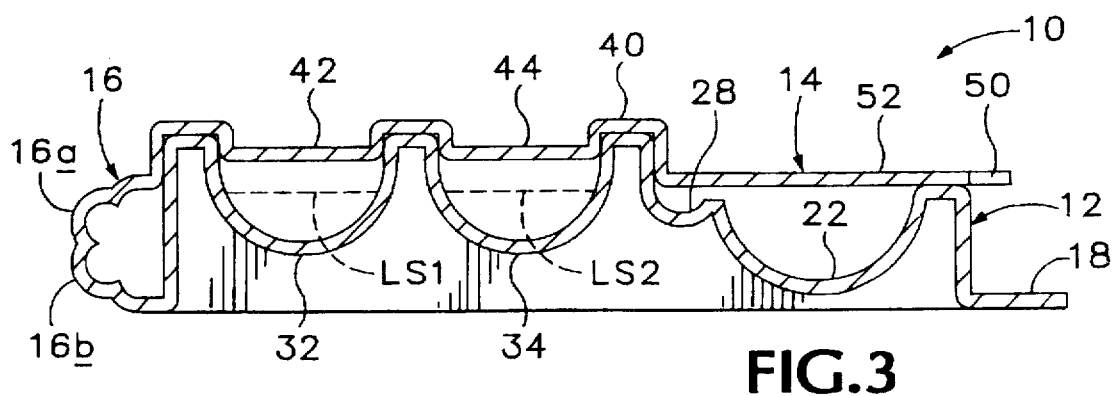
FIG. 3 is a side sectional view taken generally along lines 3—3 of FIG. 2.

FIGS. 1–3 show at 10 a dental organizer which includes a base 12 and a cover 14, each of which is opaque so as to protect onboard light-sensitive materials from exposure to light. The base and cover preferably define a unitary structure, a resilient hinge 16 being provided so as to pivotally connect the cover to the base. The hinge, in turn, provides dentists and dental technicians with the ability to open and close the organizer's cover as will be described in detail below.

In its preferred embodiment, organizer 10 is made of a light-weight, high-memory, high-density polyethylene which is chemically stable in materials such as the resins and bonding agents commonly used in a dental procedure. Alternatively, the organizer may be made of polypropylene, another material which has exhibited acceptable memory and density characteristics. The organizer may be formed by injection molding, stamping, or any other method capable of providing a device within tolerances which accommodate opening and closing of the cover as described herein.

As best shown in FIG. 1, the organizer's base preferably is a three-tiered structure, such structure including a base perimeter flange 18, a first plateau structure 20 and a second plateau structure 30. The first plateau structure defines a mixing well 22, and a plurality of elongate instrument channels 24, 26, 28. The second plateau structure defines a plurality of base storage wells 32, 34, 36, 38. Each well/channel is configured to carry a material/item used in a dental procedure, thereby providing an organizer which may be supplied with the particular materials/items necessary in performing a particular dental procedure.

Referring to FIGS. 2 and 3, cover 14 will be seen to include a hollow pedestal section 40 and a cover perimeter flange 50. The interior of the pedestal section is sized, positioned and shaped to matingly receive second plateau structure 30. The second plateau structure defines a plurality of projecting plugs 42, 44, 46, 48 which are sized, positioned and shaped to matingly seat in corresponding base storage wells. This effectively seals the base storage wells. The cover typically may be held in a closed orientation (FIGS. 2 and 3) by frictional forces between the interior walls of the pedestal section and the second plateau structure, and by frictional forces between the projecting plugs and the corresponding wells. Perimeter flange 50 surrounds the pedestal section, providing a thumb-hold by which the cover may be opened and closed. Perimeter flange 18 serves as an opposing thumb-hold.

As best shown in FIGS. 1 and 2, each instrument channel is configured to carry dental instrument for use in connection with a dental procedure which is to be performed. Typically, the instruments take the form of applicator brushes B1 and B2. Brush B1, for example, will be understood to rest in channel 24. Brush B2 similarly rests in channel 26. Channel 28 is empty in the depicted organizer but may similarly include a third brush if such brush is to be used in the procedure for which the dental organizer is prepared.

Those skilled will appreciate that the base's channels may take various forms so as to accommodate instruments of various shape and size. Channel 24, for example, includes alternative branches 24a, 24b to accommodate either a straight or bent brush. Channel 26 similarly includes alternative branches 26a, 26b. Branches 24a, 26a accommodate receipt of straight brushes. Branches 24b, 26b accommodate receipt of brushes which are bent. Each channel has a generally arcuate cross-sectional shape. Cover 14 closes with perimeter flange 50 engaging first plateau structure 20, the cover's perimeter flange thus being configured to hold the instruments in place.

As indicated by arrow 60, cover 14 opens and closes relative to the base section via a hinge which includes first and second arcuate sections 16a, 16b (FIG. 3). The cover typically is biased by the hinge toward an open orientation (shown in FIG. 1) wherein the cover is at an acute angle relative to the base. Preferably, the cover rests at a rest angle of between approximately 30-degrees and 60-degrees relative to the base. Therefore, even when open, the cover at least partially shades base storage wells 32, 34, 36, 38 from ambient light. When in the closed orientation (FIGS. 2 and 3), cover flange 50 is spaced a distance T from base flange 18, such distance corresponding to the thickness of hinge 16. This accommodates flush seating of cover flange 50 on pedestal section 20, and accommodates easy separation of the base and cover perimeter flanges so as to open the cover.

In accordance with our teachings, the base storage wells 32, 34, 36, 38 are configured to carry materials of the type commonly used in dental procedures. Such materials may be a light-sensitive bonding agents or resins, or may be etchants, priming agents, or other materials for use in a dental procedure. Light-sensitive materials LS1 and LS2 are shown illustratively in wells 32 and 34, the level of the materials being depicted by dashed lines in FIG. 3. These materials typically are poured into the wells at some time prior to beginning the procedure. Projecting plugs 42 and 44 seal the wells, thereby avoiding spillage of the materials contained therein, and avoiding exposure of such materials to light.

During a dental procedure, the materials may be mixed in mixing well 22 using an applicator brush, and then applied to the patient's teeth with the applicator brush. The applicator brush then may be discarded along with the container in order to provide a truly patient-specific dental organizer.

An upper surface 52 of flange portion 50 is of a size and character which accommodates receipt of patient information such as the patient's name, or the procedure which is to be performed. In the preferred embodiment, the upper surface takes the form of a notation surface which is configured to allow the user to transcribe a patient's name (i.e., "A. E. Jones") thereon so that the organizer later may be identified. The use of a gray dental organizer further accommodates use of the notation surface, providing a suitable surface on which markings from an indelible marker may been seen. A gray organizer also enhances the user's ability to see the light-sensitive materials which typically are tinted.

While the present invention has been shown and described with reference to the foregoing operational principles and preferred embodiment, it will be apparent to those skilled in the art that other changes in form and detail may be made therein without departing from the spirit and scope of the invention as defined in the appended claims.

We claim:

1. A dental organizer for use in carrying light-sensitive materials, said dental organizer comprising:
    an opaque base which defines a plateau structure with a plurality of wells, each being configured to contain a quantity of light-sensitive material;
    an opaque cover configured to shield with said base in a closed orientation, thereby denying light to light-sensitive materials within said wells, said cover defining a cavity configured matingly to receive said plateau structure upon positioning said cover in said closed orientation, said cover being releasably held in said closed orientation by frictional forces resulting from mating engagement of said plateau structure with said cavity; and a resilient hinge mounted intermediate said base and said cover to accommodate pivotal opening and closing of said cover relative to said base, said hinge being configured to bias said cover toward an open orientation wherein said cover at least partially shades said wells of said base from light.

2. The dental organizer of claim 1, wherein said hinge is configured to bias said cover toward an open orientation wherein said cover defines an acute angle relative to said base.

3. The dental organizer of claim 1, wherein said hinge is configured to bias said cover toward an open orientation wherein said cover and base define an angle within a range of between 30-degrees and 60-degrees.

4. The dental organizer of claim 1, wherein said cover sealably closes each of said wells when said cover is in said closed orientation.

5. The dental organizer of claim 1, wherein said cover includes a plurality of projecting plugs, each projecting plug being configured to matingly engage a corresponding well of said base upon positioning of said cover in said closed orientation to sealably close each of said wells.

6. The dental organizer of claim 5, wherein said cover is releasably held in said closed orientation by frictional forces resulting from mating engagement of said projecting plugs of said cover with said corresponding wells of said base.

7. The dental organizer of claim 1, wherein said base further defines one or more elongate channels for receiving one or more applicator brushes, said cover being configured to cover said one or more channels when in said closed orientation, and thereby, to hold said one or more applicator brushes in place.

8. A dental organizer for use in carrying light-sensitive materials of the type applied to a patient's teeth during a dental procedure, said dental organizer comprising:

an opaque base which defines a plurality of wells configured to contain quantities of light-sensitive material;

an opaque cover which matingly engages said base in a closed orientation, said cover including a plurality of projecting plugs configured to matingly engage corresponding wells of said base, said cover being releasably held in said closed orientation by frictional forces resulting from mating engagement of said projecting plugs with said corresponding wells, thereby denying light to the light-sensitive materials and sealing such light-sensitive materials within said wells; and a resilient hinge mounted intermediate said base and said cover to accommodate pivotal opening and closing of said cover relative to said base.

9. The dental organizer of claim 8, wherein said hinge is configured to bias said cover toward an open orientation wherein said cover defines an acute angle relative to said base so as to at least partially shade said wells from light.

10. The dental organizer of claim 8, wherein said hinge is configured to bias said cover toward an open orientation wherein said cover and base define an angle within a range of between 30-degrees and 60-degrees.

11. The dental organizer of claim 8, wherein said base further defines one or more elongate channels configured to receive applicator brushes, said cover being configured to cover said one or more channels when in said closed orientation, and thereby to hold the applicator brushes in place.

12. The dental organizer of claim 8, wherein said base is formed of high density polyethylene.

13. The dental organizer of claim 8, wherein the light-sensitive materials are tinted and said base is gray.

14. The dental organizer of claim 8, wherein said cover includes a notation surface on which patient information may be transcribed.

15. A patient-specific dental organizer for use in carrying light-sensitive materials and corresponding applicator brushes whereby such light-sensitive materials are applied to a patient's teeth, said dental organizer comprising:

an opaque base which defines a plurality of wells configured to contain quantities of light-sensitive material and one or more elongate channels configured to receive the applicator brushes;

an opaque cover which matingly engages said base in a closed orientation, said cover including a plurality of projecting plugs configured to matingly engage corresponding wells of said base, said cover being releasably held in said closed orientation by frictional forces resulting from mating engagement of said projecting plugs of said cover with said corresponding wells of said base, thereby denying light to the light-sensitive materials, sealing said wells to prevent spillage, and covering said channels to hold the applicator brushes in place; and a resilient hinge mounted intermediate said base and said cover to accommodate pivotal opening and closing of said cover relative to said base, said hinge being configured to bias said cover toward an open orientation wherein said cover defines an acute angle relative to said base so as to at least partially shade the light-sensitive materials from light.

16. The dental organizer of claim 15, wherein said hinge is configured to bias said cover toward an open orientation wherein said cover and base define an angle within a range of between 30-degrees and 60-degrees.

17. The dental organizer of claim 15, wherein said cover includes a notation surface on which patient information may be transcribed.

18. The dental organizer of claim 15, wherein said base includes a plateau structure and said cover defines a cavity configured matingly to receive said plateau structure upon positioning said cover in said closed orientation, said cover being releasably held in said closed orientation by frictional forces resulting from mating engagement of said plateau structure with said cavity.

* * * * *